United States Patent
Chou et al.

(10) Patent No.: US 11,709,162 B2
(45) Date of Patent: Jul. 25, 2023

(54) HOMOGENEOUS ASSAY WITH PARTICLE AGGREGATION OR DE-AGGREGATION

(71) Applicant: Essenlix Corporation, Monmouth Junction, NJ (US)

(72) Inventors: Stephen Y. Chou, Princeton, NJ (US); Wei Ding, Princeton, NJ (US); Ji Li, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 17 days.

(21) Appl. No.: 17/268,567

(22) PCT Filed: Aug. 16, 2019

(86) PCT No.: PCT/US2019/046949
§ 371 (c)(1),
(2) Date: Feb. 15, 2021

(87) PCT Pub. No.: WO2020/037289
PCT Pub. Date: Feb. 20, 2020

(65) Prior Publication Data
US 2021/0255177 A1    Aug. 19, 2021

Related U.S. Application Data

(60) Provisional application No. 62/719,062, filed on Aug. 16, 2018.

(51) Int. Cl.
*G01N 33/543* (2006.01)
*G01N 15/02* (2006.01)

(52) U.S. Cl.
CPC ... *G01N 33/54313* (2013.01); *G01N 15/0227* (2013.01); *G01N 33/54373* (2013.01); *G01N 2015/025* (2013.01)

(58) Field of Classification Search
CPC ......... G01N 33/54313; G01N 15/0227; G01N 33/54373; G01N 2015/025
USPC .......................................................... 435/5
See application file for complete search history.

(56) References Cited

U.S. PATENT DOCUMENTS

| | | | | |
|---|---|---|---|---|
| 5,583,003 A | * | 12/1996 | Hillyard | G01N 33/6854 435/7.25 |
| 2003/0215810 A1 | | 11/2003 | Lu et al. | |
| 2005/0232888 A1 | * | 10/2005 | Weber | A61K 8/0295 424/70.12 |

(Continued)

FOREIGN PATENT DOCUMENTS

| | | |
|---|---|---|
| WO | 2002023154 A2 | 3/2002 |
| WO | 2017048871 A1 | 3/2017 |
| WO | 2019027963 A1 | 2/2019 |

OTHER PUBLICATIONS

International Preliminary Report on Patentability for PCT/US2019/046949 established by IPEA/US completed on Nov. 20, 2020.

(Continued)

*Primary Examiner* — Tarifur R Chowdhury
*Assistant Examiner* — Omar H Nixon

(57) ABSTRACT

Disclosed are devices and methods for performing biological and chemical assays, such as immunoassays and nucleic acid assays, more particularly a homogeneous assay that does not use a wash step by using the aggregation and de-aggregation processes of microparticles or nanoparticles.

66 Claims, 6 Drawing Sheets

A

B

(56) References Cited

U.S. PATENT DOCUMENTS

2010/0065726 A1* 3/2010 Zhong .............. G01N 21/6454
                                                        250/227.24
2012/0149587 A1* 6/2012 Landers ............ G01R 33/1269
                                                         435/6.12

OTHER PUBLICATIONS

Written Opinion of the International Searching authority for PCT/US2019/046949 established by ISA/US completed on Oct. 28, 2019.

* cited by examiner

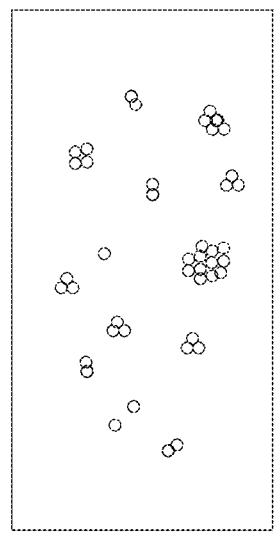
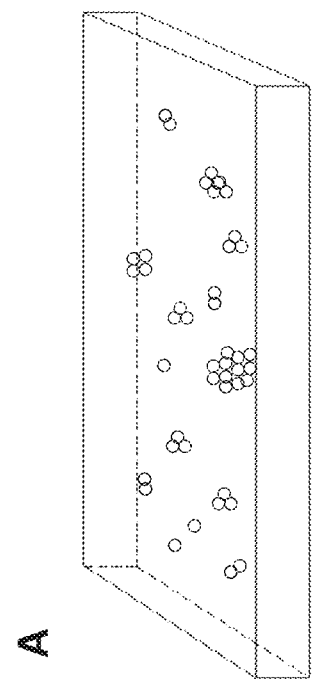
Fig. 1

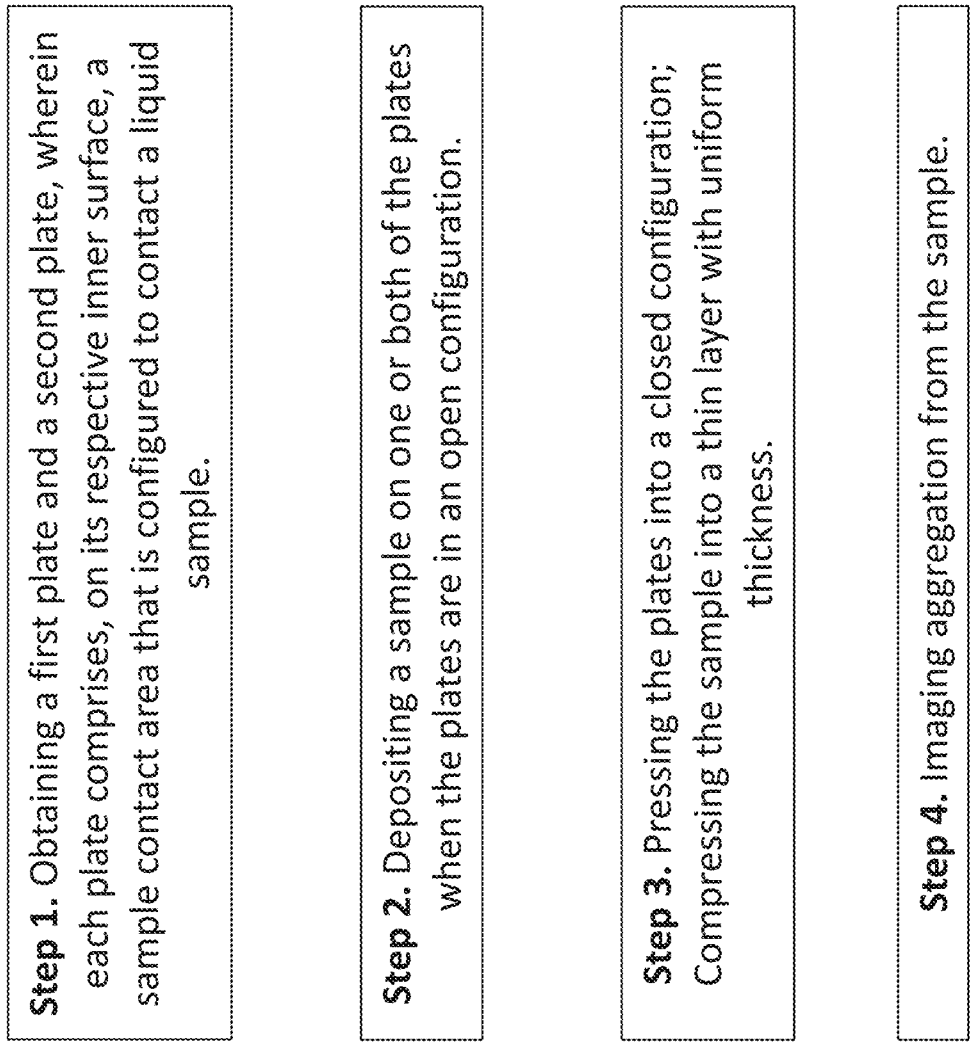

Step 1. Obtaining a first plate and a second plate, wherein each plate comprises, on its respective inner surface, a sample contact area that is configured to contact a liquid sample.

Step 2. Depositing a sample on one or both of the plates when the plates are in an open configuration.

Step 3. Pressing the plates into a closed configuration; Compressing the sample into a thin layer with uniform thickness.

Step 4. Imaging aggregation from the sample.

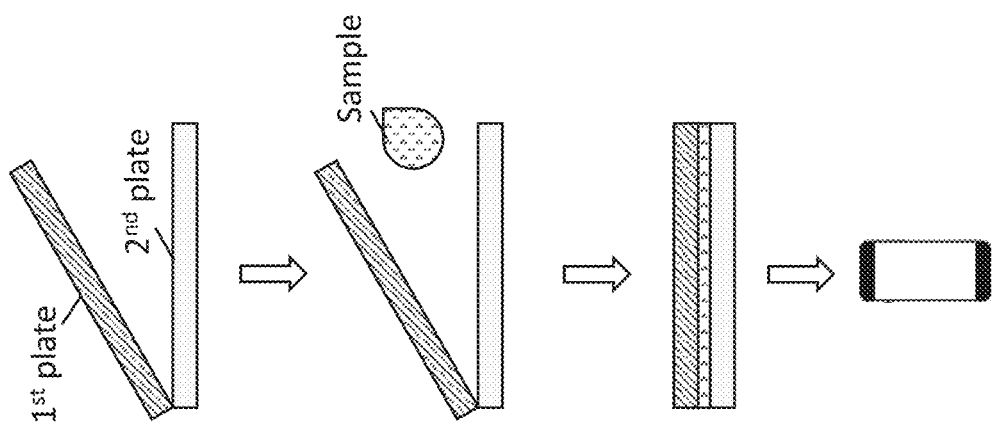

Fig. 3

HOMOGENEOUS ASSAY WITH PARTICLE AGGREGATION OR DE-AGGREGATION

CROSS-REFERENCE TO RELATED APPLICATIONS

This application is a National Stage entry (§ 371) application of International Application No. PCT/US2019/046949, filed on Aug. 16, 2019, which claims the benefit of priority of U.S. Provisional Patent Application No. 62/719,062, filed on Aug. 16, 2018, the contents of which is relied upon and incorporated herein by reference in its entirety. The entire disclosure of any publication or patent document mentioned herein is entirely incorporated by reference.

FIELD

The present disclosure is related to devices and methods of performing biological and chemical assays, such as immunoassays and nucleic assay acid.

BACKGROUND

In biological and chemical assays (e.g., diagnostic testing), often a homogeneous assay, which does not need to wash, is preferred. The disclosure provides devices and methods for achieving these goals.

SUMMARY

In one or more embodiments, the disclosure provides a device and method for a homogenous assay with particle aggregation caused by an analyte, a device and method for a homogenous assay with particle de-aggregation caused by an analyte, and a system for measuring aggregated or de-aggregated particles that are caused by an analyte.

BRIEF DESCRIPTION OF THE DRAWINGS

The drawings are for illustration purposes only. The drawings may or may not be to scale.

FIG. 1 shows an exemplary embodiment where certain particles have aggregated in a liquid sample.

FIG. 3 shows an exemplary flow chart and illustrates the process of the disclosed aggregation particle assay.

DETAILED DESCRIPTION OF EXEMPLARY EMBODIMENTS

Figure 2:
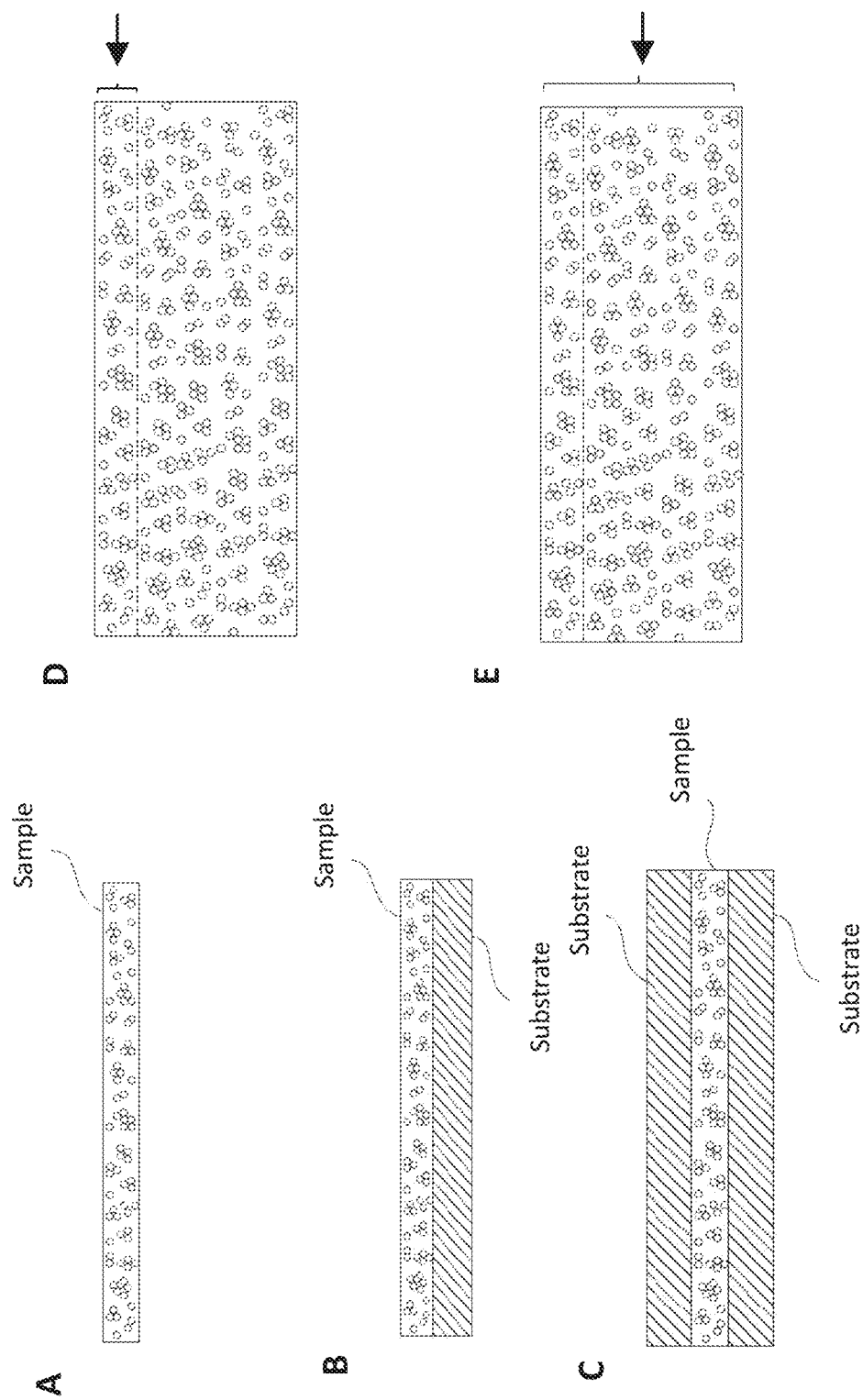
FIG. 2 shows several exemplary embodiments of how the sample is imaged and analyzed to obtain optimal results.

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the disclosure.

One objective of the disclosure is to perform a homogeneous assay in "one step". The "one step" assay means that in assaying, one drops a sample in the assay and then reads the signal, and there are no other steps in between (e.g., no washing between steps). The assays include, for example, protein assays and nucleic acid assays.

One aspect of the disclosure is to allow performing a homogeneous assay in "one-step" without using any washing. In the "one-step" assay, it uses two plates that are movable relative to each other, a sample with an analyte is dropped on one or both of the plates, the two plates are pressed against each other to compress at least a portion of the sample into a thin layer, followed by reading the signal from the plate without any washing.

Another significant feature of the can be, for example, is that in certain embodiments, the two plates of the assay are pressed by human hands, and by using particular set of the plates and the spacers, as specified herein, at least a portion of the sample have a uniform thickness.

To achieve a one-step assay that detects an analyte in a sample, a key approach of the disclosure is by making the particles in solution aggregate and/or de-aggregate after adding the analyte, then either the image or the lump-sum optical signal is used to analyze the analyte in the assay.

In an embodiment the disclosure provides a device for homogenous assay with particles aggregation, comprising: a first plate, a second plate, and spacers, wherein:
i. the plates are movable relative to each other into different configurations, including an open configuration and a closed configuration;
ii. each of the plates has, on its respective inner surface, a sample contact area for contacting a sample that contains or is suspected to contain an analyte;
iii. one or both of the plates comprise, inside the sample contact area, one or more spacers of predetermined substantially uniform height; and
iv. one or both of the plates comprise, on the respective inner surface, a plurality of separated particles, wherein the particles have capture agents immobilized thereon, wherein the capture agents are capable of binding to and immobilizing the analyte and causing, after binding to the analyte, an aggregation of the separated particles;
wherein in the open configuration, the two plates are partially or entirely the separated apart, the spacing between the plates is not regulated by the spacers, and the sample is deposited on one or both of the plates; and
wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers.

In an embodiment the disclosure provides a device for a homogenous assay with particles aggregation, comprising: a first plate, a second plate, and spacers, wherein:
i. the plates are movable relative to each other into different configurations, including an open configuration and a closed configuration;
ii. each of the plates has, on its respective inner surface, a sample contact area for contacting a sample that contains or is suspected to contain an analyte;
iii. one or both of the plates comprise, inside the sample contact area, one or more spacers of predetermined substantially uniform height; and
iv. one or both of the plates comprise, on the respective inner surface, a plurality of aggregated particles, wherein the particles have binding agents connected to each other; and wherein the analyte can de-aggregate the aggregated particles when the analyte in contact with the particles;

wherein in the open configuration, the two plates are partially or entirely separated apart, the spacing between the plates is not regulated by the spacers, and the sample is deposited on one or both of the plates; and wherein in the closed configuration, which is configured after deposition of the sample in the open configuration: at least part of the sample is compressed by the two plates into a layer of highly uniform thickness, the uniform thickness of the layer is confined by the inner surfaces of the plates and is regulated by the plates and the spacers.

In an embodiment the disclosure provides a system for measuring aggregated particles or de-aggregated particles that are caused by an analyte, comprising, any of a prior device, a light source that emits light, and an imager, wherein the imager is configured to measure the light that transmits through, scattered from, or reflected from the aggregated, or any combination of thereof.

In an embodiment the disclosure provides a method of performing a homogenous assay with particle aggregation, comprising the steps of:

(a) obtaining a sample suspected of containing an analyte;
(b) obtaining a first plate and a second plate, wherein:
  i. the plates are movable relative to each other into different configurations, including an open configuration and a closed configuration;
  ii. each of the plates has, on its respective inner surface, a sample contact area for contacting the sample;
  iii. one or both of the plates comprise spacers, at least one of the spacers is inside the sample contact area, and the spacers have a predetermined substantially uniform height; and
  iv. one or both of the plates comprise, on the respective inner surface, a plurality of separated particles or aggregated particles;
(c) depositing the sample on one or both of the plates when the plates in the open configuration, wherein the two plates are partially or entirely separated apart and the spacing between the plates is not regulated by the spacers;
(d) after (c), bringing the two plates together and pressing the plates into the closed configuration, wherein at least part of the sample is compressed by the two plates into a layer of highly uniform thickness, the uniform thickness of the layer is confined by the inner surfaces of the two plates and is regulated by the spacers and the plates; and
(e) while the plates are at the closed configuration, detecting and analyzing the particles in the layer of uniform thickness by image or lump sum optical signal.

The device and method of any prior embodiments, wherein the particles are different in their optical properties selected from the group consisting of: photoluminescence, electroluminescence, and electrochemiluminescence, light absorption, reflection, transmission, diffraction, scattering, diffusion, surface Raman scattering, and any combination thereof.

In the device and method of any prior embodiments, the particles in the disclosure can be, for example, biological/nonbiological, organic/non-organic, magnetic/non-magnetic, metallic/non-metallic, or light-emitting/non-emitting.

In some embodiments, the particles include natural particles or man-made particles, or a combination or mixture thereof. For example, the particles include natural biological entities, such as but not limited to cells, cell fragments, macromolecules (e.g., polysaccharides, proteins, or nucleic acids), cell congregates, tissues, or virus particles. In some embodiments, the particles include man-made objects such as but not limited to polymer particles, metal particles, magnetic particles, or semiconductor particles, or a combination or mixtures thereof.

In some embodiments, the particles (e.g., beads) of the disclosure can include a polymer, such as but not limited to polystyrene, polypropylene, polycarbonate, latex, or any combinations thereof.

In some embodiments, the particles (e.g., beads) of the disclosure include a metal, such as but not limited to gold, silver, copper, and platinum.

In some embodiments, the particles (e.g., beads) of the disclosure include gold nanoparticles, gold nanoshell, gold nanotubes, and others.

In some embodiments, the particles (e.g., beads) of the disclosure include a semiconductor, such as but not limited to CdSe, CdS, and CdS or CdSe coated with ZnS. In some embodiments, the particles (e.g., beads) of the disclosure can include a magnetic material, such as but not limited to ferromagnetite, and magnetized ZnS, ZnO, TiO2, AgI, AgBr, HgI2, PbS, PbSe, ZnTe, CdTe, In2S3, In2Se3, Cd3P2, Cd3As2, InAs, and GaAs.

In some embodiments, the particles can have any shape, e.g., spheres (generally referred to as beads) or rods, or irregular shapes, and a population of particles can have particles that have the same size and size or particles that have varying shapes or sizes. The particles can be nanoparticles that have a size (mean diameter for rods or spheres) in the nanometer level; the particles can be microparticles that have a size in the micrometer level. In some embodiments, beads in a population of beads can have a uniform diameter or different diameters.

In some embodiments, the size of the particles can be from about 5 nm to about 10 um. In some embodiments, the size of the particles is less than 2 nm, 5 nm, 10 nm, 20 nm, 50 nm, 100 nm, 200 nm, 500 nm, 1 um, 2 um, 5 um, 10 um, 20 um, 50 um, 100 um, 200 um, 500 um, 1 mm, 2 mm, 5 mm, 10 mm, 20 mm, 50 mm, or 100 mm, or in a range between any of the two values. In some embodiments, the beads can have size of 100 nm, 500 nm, 1 μm, 5 μm, 50 μm, 500 μm, 1 mm or in a range between any two of the values, and a preferred range of 1 μm to 10 μm.

In some embodiments, the preferred size of the particles are from about 5 nm to about 10 nm.

In some embodiments, the preferred size of the particles is from about 10 nm to about 50 nm.

In some embodiments, the preferred size of the particles is from about 50 nm to about 100 nm.

In some embodiments, the preferred size of the particles is from about 100 nm to about 500 nm.

In some embodiments, the preferred size of the particles is from about 500 nm to about 1000 nm.

In some embodiments, the preferred size of the particles is from about 1 um to about 5 um.

In some embodiments, the preferred size of the particles is from about 5 um to about 10 um.

In some embodiments, the size of the particles is less than 2 nm, 5 nm, 10 nm, 20 nm, 50 nm, 100 nm, 200 nm, 500 nm, 1 um, 2 um, 5 um, 10 um, 20 um, 50 um, 100 um, 200 um, 500 um, 1 mm, 2 mm, 5 mm, 10 mm, 20 mm, 50 mm, or 100 mm, or in a range between any of the two values. In some embodiments, the beads can have size of 100 nm, 500 nm, 1 μm, 5 μm, 50 μm, 500 μm, 1 mm or in a range between any two of the values, and a preferred range of 1 μm to 10 μm.

The spacer height, the spacing between the plates, and/or sample thickness is between 1.5 um to 2.5 um in one preferred embodiment.

The spacer height, the spacing between the plates, and/or sample thickness is between 2.5 um to 4 um in one preferred embodiment.

The spacer height, the spacing between the plates, and/or sample thickness is between 4 um to 6 um in one preferred embodiment.

The spacer height, the spacing between the plates, and/or sample thickness is between 6 um to 10 um in one preferred embodiment.

The spacer height, the spacing between the plates, and/or sample thickness is between 10 um to 15 um in one preferred embodiment.

The spacer height, the spacing between the plates, and/or sample thickness is between 15 um to 25 um in one preferred embodiment.

The spacer height, the spacing between the plates, and/or sample thickness is between 25 um to 35 um in one preferred embodiment.

The spacer height, the spacing between the plates, and/or sample thickness is between 35 um to 50 um in one preferred embodiment.

The spacer height, the spacing between the plates, and/or sample thickness is between 50 um to 100 um in one preferred embodiment.

The spacer height, the spacing between the plates, and/or sample thickness is between 100 um to 150 um in one preferred embodiment.

The spacer height, the spacing between the plates, and/or sample thickness is between 150 um to 200 um in one preferred embodiment.

In some embodiments, besides the binding agents, the particles are coated or derivatized with agents to enhance binding of a selected analyte. For example, particles can include a silica coating or be derivatized with streptavidin.

In some embodiments, the aggregation of the particles of the disclosure can be induced by binding between the particles or between agents that are positioned on the surface of the particles.

In some embodiments, the binding of the agents are the results of biological, biochemical, chemical, or physical (e.g. magnetic) effects. For example, the binding between the agents can be an antibody-antigen binding, a complimentary binding of nucleic acids (e.g. complimentary strands of DNA, RNA, or other nucleic acids), a binding between an catalyst and its substrate, a binding or aptamer against its target, a binding of RNA interference sequence against its target, a ligand-receptor binding, or a binding between an agent and its agonist or antagonist.

In some embodiments, the aggregation happens naturally or with induction, e.g. with conjugation of binding agents to the particles.

In some embodiments, before contacting the analyte, close to 100% of the particles in the sample are aggregated. In some embodiments, before contacting the analyte, the percentage of particles that aggregate is more than 10%, 20%, 30%, 40%, 50%, 60%, 70%, 80%, 90%, 95%, or 99%, or in a range between any of the two values. In certain embodiments, before contacting the analyte, the percentage of particles that aggregate is more than 60%, 70%, 80%, 90%, 95%, or 99%, or in a range between any of the two values.

In some embodiments, after contacting the analyte, close to 100% of the particles in the sample are aggregated. In some embodiments, after contacting the analyte, the percentage of particles that aggregate is more than 10%, 20%, 30%, 40%, 50%, 60%, 70%, 80%, 90%, 95%, or 99%, or in a range between any of the two values. In certain embodiments, after contacting the analyte, the percentage of particles that aggregate is more than 60%, 70%, 80%, 90%, 95%, or 99%, or in a range between any of the two values.

Referring to the figures, FIG. 1 shows an exemplary embodiment of the present invention, where certain particles have aggregated in a liquid sample. Panel (A) of FIG. 1 shows a prospective view and panel (B) shows a top view of a liquid sample. As shown in FIG. 1, the particles can aggregate to different levels, resulting in different aggregate size and different signal strength from the aggregates.

In some embodiments, the sample is imaged, and the images are analyzed to measure the concentration of a target analyte.

In some embodiments, the sample is imaged, and the particle aggregations in the image are counted, sized and analyzed to measure the concentration of a target analyte.

In some embodiments, the sample is imaged, and the single particle and the particle aggregations in the image are counted, sized and analyzed to measure the concentration of a target analyte.

In some embodiments, the sample is not imaged, but the lump-sum optical signal through the device such as transmittance, absorptance, absorptance wavelength shift, color is analyzed to measure the concentration of a target analyte.

In certain embodiments, the aggregation is increased with the increase of analyte concentration.

In certain embodiments, the aggregation is decreased with the increase of analyte concentration.

In some embodiments, a higher concentration of the analyte can result in larger aggregate size. For example, while more particles do not aggregate (resulting in aggregates that include only one particle) or only modestly aggregate (resulting in aggregates that include a small number of particles, e.g., 2 or 3) when the analyte is at a low concentration, a higher concentration of the analyte induces more aggregation, e.g. resulting in more large aggregates, which include a higher average number of particles in each aggregate.

FIG. 2 shows several exemplary embodiments of how the sample is imaged and analyzed to obtain optimal results. In panel (A) of FIG. 2, the sample is in a thin layer but not attached to any plate; in panel (B) of FIG. 2, the sample is in a thin layer that is on a plate; in panel (C) of FIG. 2, the sample is in a thin layer that is compressed between two plates (e.g., a first plate and a second plate of a QMAX device).

FIG. 2 shows the sample preparation and imaging method: (A) The sample is in a thin layer but not attached to any plate; (B) The sample is in a thin layer that is on a plate; (C) The sample is in a thin layer that is compressed between two plates; (D) An imaging device can capture one or more images of a layer of the sample (arrow indicates imager positioning; not shown); and (E) The sample can be imaged by a three-dimensional (3-D) scanning technology that captures all the aggregates in the entire thickness of the sample (arrow indicates imager positioning; not shown).

FIG. 3 shows an exemplary flow chart and illustrates the process of the disclosed aggregation particle assay.

Figure 4:
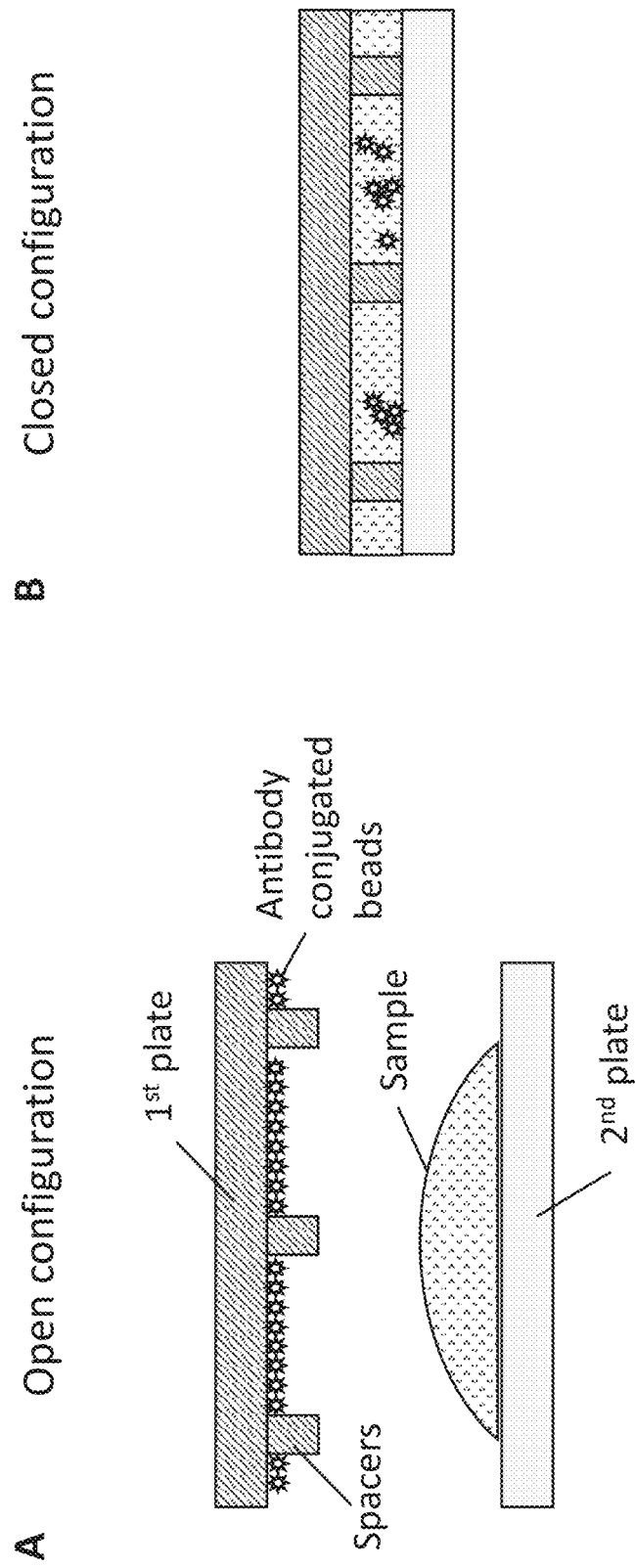
FIG. 4 shows open and closed plate configurations for an aggregation particle assay.

FIG. 4 shows open and closed plate configuration for an aggregation particle assay: A) is in an open configuration where a first plate is coated with antibody conjugated beads; and B) is in the closed configuration. When sample is added, the two plates are closed. Beads form aggregates in the presence of analyte from the sample.

Figure 5:
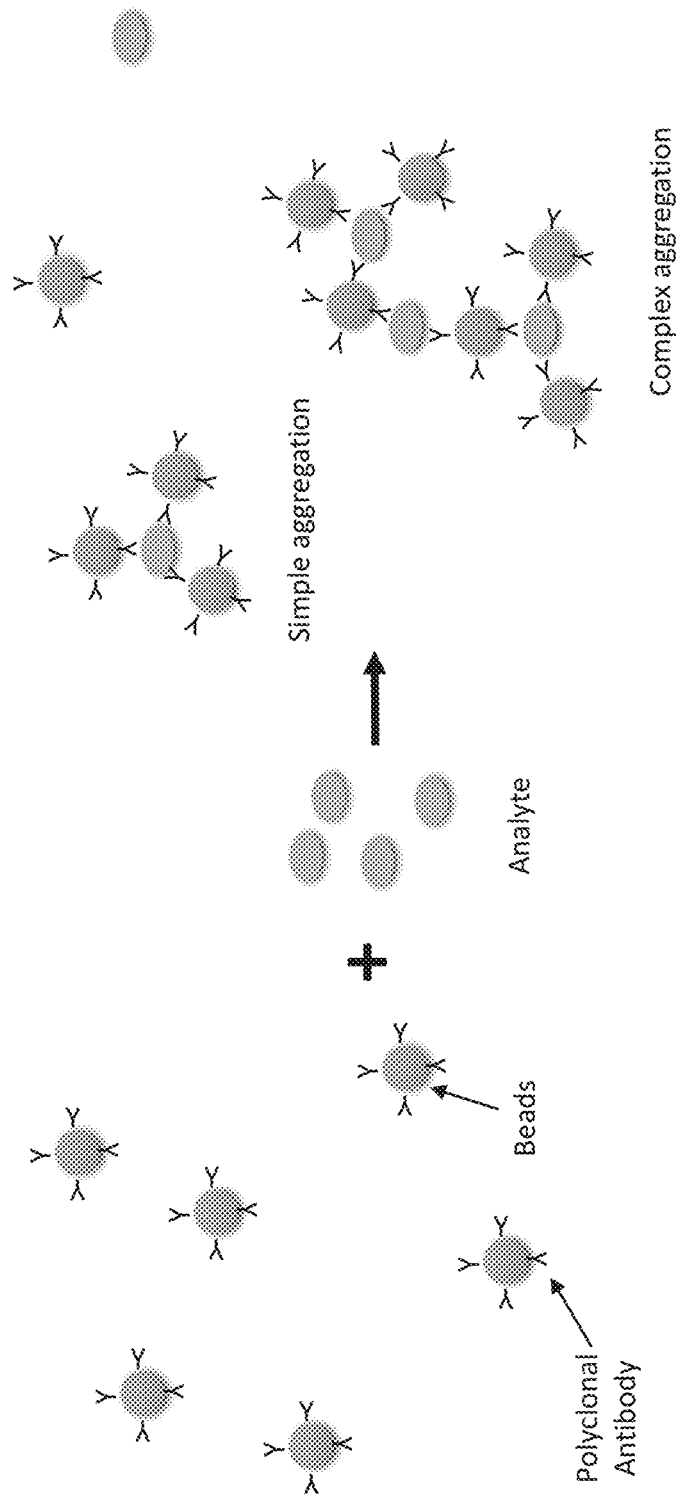
FIG. 5 shows biochemistry of aggregation particle assay.

FIG. 5 shows biochemistry of an aggregation particle assay. Beads are coated with polyclonal antibody. In the presence of the analyte, multiple epitopes on the analyte can be bound to the polyclonal antibody to form either simple single aggregation or complex aggregation.

In some embodiments, antibody coated on the particles can be, for example, one type of polyclonal antibody, a mixture of polyclonal antibodies, or mixture of monoclonal antibodies, or mixture of monoclonal antibody and polyclonal antibody.

In some embodiments, the binding between the agents in the assay can be, for example, an antibody-antigen binding, a complimentary binding of nucleic acids (e.g., complimentary strands of DNA, RNA, or other nucleic acids), a binding between an catalyst and its substrate, a binding or aptamer against its target, a binding of RNA interference sequence against its target, a ligand-receptor binding, or a binding between an agent and its agonist or antagonist.

In some embodiments, the aggregation of particles can be, for example, induced by adding an agonist.

In some embodiments, the aggregation of particles can be, for example, reversed by adding an antagonist.

In some embodiments, the imaging area can be, for example, a single layer, multiplex layers, or the whole 3D space of the liquid sample.

In some embodiments, the imaging can be accomplished, for example, with aggregation in bright field or plasmonic resonance shift.

In some embodiments, if the thickness of the sample is less than a predetermined value (e.g., 0.5 um, 1 um, 2 um, 5 um, or 10 um) or if a ratio between the thickness of the sample and the size of the particle is less than a predetermined value (e.g., 50, 20, 10, 5, or 2 microns), the sample can be imaged directly because any significant overlapping of aggregates in the sample is unlikely. Such overlapping depends on the thickness of the sample and the ratio between the thickness of the sample and the size of the particle. When the thickness is low and/or when the ratio is low, the likelihood of overlapping is also low. In some embodiments, the ratio can be, for example, less than 1000, 500, 200, 100, 50, 20, 10, 9, 8, 7, 6, 5, 4, 3, 2, 1.5, or 1.2, or in a range between any of the two values.

In some embodiments, to improve the accuracy of results, more than a certain percentage of the lateral area of the sample needs to be imaged.

For example, in some embodiments, the ratio of the imaged area versus total sample area can be, for example, more than 1%, 2%, 5%, 10%, 15%, 20%, 25%, 30%, 35%, 40%, 45%, or 50%, or in a range between any of the two values. In certain embodiments, the ratio of the imaged area versus total sample area can be, for example, in the range of about 1% and about 10%.

In FIG. 2 panels (D) and (E) the sample has thickness that is more than a predetermined value (e.g., 10 um, 20 um, 50 um, or 100 um). In some embodiments, when the sample thickness is more than the predetermined value, or when the ratio between the thickness of the sample and the size of the particle is higher than a predetermined value (e.g. 10, 20, 50, or 100), the imaging of the sample and the measurement of the analyte can take an alternative approach. For example, as shown in panel (D) of FIG. 2, an imaging device can capture one or more images of a layer of the sample, wherein the images can be used to assess the overall concentration of the analyte in the sample. In certain embodiments, as shown in panel (E) of FIG. 2, the sample can be imaged by a three-dimensional (3-D) scanning technology that captures all the aggregates in the entire thickness of the sample without discounting any overlapping. The 3-D scanning technology used in the present invention can be any contact or non-contact 3-D technology that produces an overall scanning result of the sample. For example, the 3-D scanning technology can be time-of-flight scanning or triangulation scanning, or any variation or improvements thereof.

Other Principles and Methods:

In some embodiments, the aggregation assay can use, for example, gold nano- or micro-particles to form aggregations via binding to analyte.

In some embodiments, the gold particles are coated with agents that have binding affinity to the target analyte. The size of the particles can be, for example, from about 5 nm to about 10 μm. The shape can be, for example, spheres (generally referred to as beads) or rods, or irregular shapes, and a population of particles can have particles that have the same shape and size, or particles that have varying shapes or sizes.

In some embodiments, the coating can be, for example, accomplished by covalent bond or passive absorption. The gold particle can be, for example, of pure gold or having a gold shell surrounding core particles of other materials such as latex or silica. The thickness of gold shell can be from about 1 nm to about 10 μm.

In some embodiments, the coated gold particles can be printed or sprayed and dried on QMAX card.

In some embodiments, the aggregation can be formed as follows: A liquid sample is added on QMAX card and the card is closed. The deposited gold particles are released from the QMAX card in the liquid. If the sample contains target analyte, coated gold particles can bind to the target at multiple location on the surface of the target and form aggregates. The aggregation can be a simple aggregation in which multiple gold particles bind to a single analyte, or a complex aggregation in which a "network" is formed between multiple gold particles and multiple analytes.

In some embodiments, the formed aggregation of particles can be imaged, for example, at visible wavelength or designated wavelength range.

In some embodiments, the analyte concentration and aggregation of particles can be, for example, analyzed from the wavelength shift from the particles.

In some embodiment, the analyte concentration and aggregation of particles can be analyzed, for example, from the size of aggregated particles.

In some embodiments, the analyte concentration and aggregation of particles can be analyzed, for example, from the size of de-aggregated particles.

In some embodiments, the color (absorption wavelength range, fluorescence wavelength range), size and number of aggregates can be determined by image analysis.

In some embodiments, alternatively, the size or aggregation can be, for example, determined by the shift of plasmonic resonance of the gold particle aggregations.

In some embodiments, in de-aggregation assay, existing particle aggregations are dissociated in the presence of analyte.

In some embodiments, particles are coated with agents that have binding affinity to a specific reagent. The coated gold particles are pre-mixed with the specific reagent so that aggregation is already formed before assay.

In some embodiments, the nature of dissociation of aggregation by the target analyte can be cleavage of the pre-bound reagent (e.g., enzymic cleavage of nucleic acid), removal or destroying the pre-binding agents (e.g., denature of pre-bound protein), or competition with the pre-bound reagent. When such analyte is present in the sample, the pre-formed aggregation will be dissociated.

In some embodiments, the dissociation of aggregation can be accomplished, for example, by removal or destroying the pre-binding agents (e.g., denature of pre-bound protein).

The device, kit, system, smartphone system, and method of any prior embodiments, wherein the particles are made of a material selected from the group consisting of: polystyrene, polypropylene, polycarbonate, PMMG, PC, COC, COP, glass, resin, aluminum, gold or other metal or any other material whose surface can be modified to be associated with the capture agent.

The device, kit, system, smartphone system, and method of any prior embodiments, wherein the beads are treated with a protein stabilizer.

The device, kit, system, smartphone system, and method of any prior embodiments, wherein the capture agent is conjugated with the beads.

The device, kit, system, smartphone system, and method of any prior embodiments, wherein the beads are prepared by: activating with N-Hydroxysuccinimide (NETS); blocking with a BSA solution; and incubating with a capture agent solution.

The device, kit, system, and method of any prior embodiments, wherein the liquid sample is made from a biological sample selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

The device, kit, system, smartphone system, and method of any prior embodiments, wherein the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

EXAMPLE

Homogeneous Particles Aggregation—for Human CRP (C-Reactive Protein)

Here we describe an experiment of homogeneous QMAX immunoassay for human CRP according to one embodiment of the disclosure.

In this experiment, the device for the immunoassay comprises a first plate and a second plate. Conventional glass slide was used as the first plate and an X-plate with a 10 μm spacer was used as the second plate, as shown in FIG. 4. An iPhone with a bright field adapter was used as the detector.

The experiment was conducted according to the following procedures:
1. Antibody conjugation. Rabbit polyclonal anti-CRP (Abcam) was conjugated to 2 μm Protein A polystyrene beads (Invitrogen) according to manufacturer's manual. The conjugated beads were then blocked by 4% BSA in PBS overnight at 4° C.
2. Coating plate. 1 μL of conjugated bead was dropped and air-dried on substrate card of Q-card.
3. Adding sample. 3 μL of CRP solution (in PBS) with different concentrations was added on the substrate card and then covered by X-plate (2 μm pillar height).
4. Imaging. After 1 min, the bright field of Q-card was imaged by iPhone 6s and bright field adapter.

Figure 6:
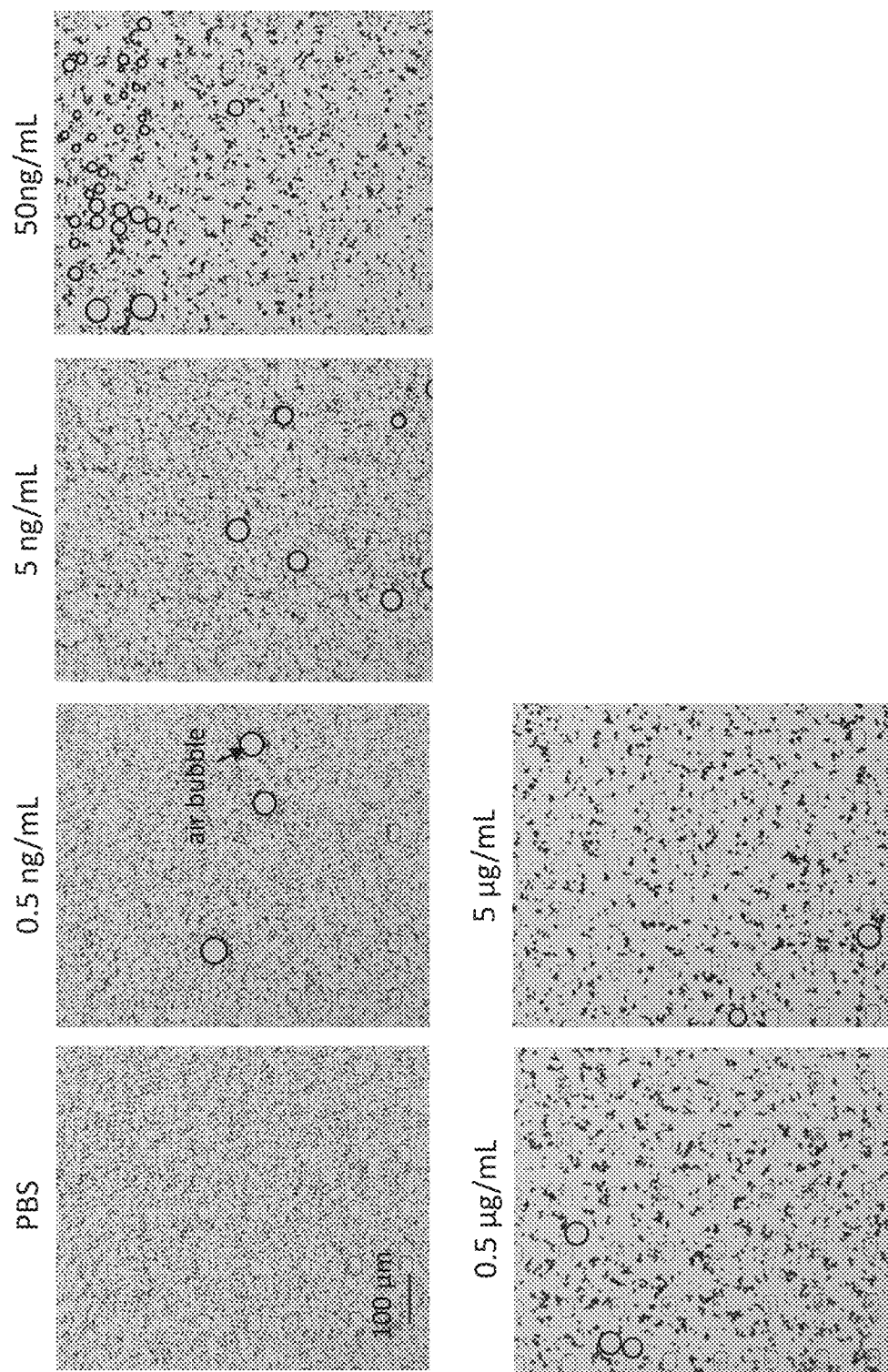
FIG. 6 shows images from a CRP aggregation particle assay.

FIG. 6 shows images from a CRP aggregation particle assay. Different concentrations of CRP were tested, and bright field images were taken after 1 min. Note that the aggregation size clearly correlates with analyte concentration.

Compressed Regulated Open Flow" (CROF)

In assaying, a manipulation of a sample or a reagent can lead to improvements in the assaying. The manipulation includes, but not limited to, manipulating the geometric shape and location of a sample and/or a reagent, a mixing or a binding of a sample and a reagent, and a contact area of a sample of reagent to a plate.

Many embodiments of the present invention manipulate the geometric size, location, contact areas, and mixing of a sample and/or a reagent using a method, termed "compressed regulated open flow (CROF)", and a device that performs CROF.

The term "compressed open flow (COF)" refers to a method that changes the shape of a flowable sample deposited on a plate by (i) placing other plate on top of at least a part of the sample and (ii) then compressing the sample between two plates by pushing the two plates towards each other; wherein the compression reduces a thickness of at least a part of the sample and makes the sample flow into open spaces between the plates.

The term "compressed regulated open flow" or "CROF" (or "self-calibrated compressed open flow" or "SCOF" or "SCCOF") refers to a particular type of COF, wherein the final thickness of a part or entire sample after the compression is "regulated" by spacers, wherein the spacers, that are placed between the two plates.

The term "the final thickness of a part or entire sample is regulated by spacers" in a CROF means that during a CROF, once a specific sample thickness is reached, the relative movement of the two plates and hence the change of sample thickness stop, wherein the specific thickness is determined by the spacer.

One embodiment of the method of CROF, comprises:
(a) obtaining a sample, that is flowable;
(b) obtaining a first plate and a second plate that are movable relative to each other into different configurations, wherein each plate has a sample contact surface that is substantially planar, wherein one or both of the plates comprise spacers and the spacers have a predetermined height, and the spacers are on a respective sample contacting surface;
(c) depositing, when the plates are configured in an open configuration, the sample on one or both of the plates; wherein the open configuration is a configuration in which the two plates are either partially or completely separated apart and the spacing between the plates is not regulated by the spacers; and
(d) after (c), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers, wherein the relevant volume is at least a portion of an entire volume of the sample, and wherein during the sample spreading, the sample flows laterally between the two plates.

The term "plate" refers to, unless being specified otherwise, the plate used in a CROF process, which a solid that has a surface that can be used, together with another plate, to compress a sample placed between the two plate to reduce a thickness of the sample.

The term "the plates" or "the pair of the plates" refers to the two plates in a CROF process.

The term "first plate" or "second plate" refers to the plate use in a CROF process.

The term "the plates are facing each other" refers to the cases where a pair of plates are at least partially facing each other.

The term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value. There are two types of the spacers: "open-spacers" and "enclosed-spacers".

The term "open-spacer" means the spacer have a shape that allows a liquid to flow around the entire perimeter of the spacer and flow pass the spacer. For example, a pillar is an open spacer.

The term of "enclosed spacer" means the spacer of having a shape that a liquid cannot flow abound the entire perimeter of the spacer and cannot flow pass the spacer. For example, a ring shape spacer is an enclosed spacer for a liquid inside the ring, where the liquid inside the ring spacer remains inside the ring and cannot go to outside (outside perimeter).

The term "a spacer has a predetermined height" and "spacers have predetermined inter-spacer distance" means, respectively, that the value of the spacer height and the inter spacer distance is known prior to a CROF process. It is not predetermined, if the value of the spacer height and the inter-spacer distance is not known prior to a CROF process. For example, in the case that beads are sprayed on a plate as spacers, where beads are landed on random locations of the plate, the inter-spacer distance is not predetermined. Another example of not predetermined inter spacer distance is that the spacers moves during a CROF processes.

The term "a spacer is fixed on its respective plate" in a CROF process means that the spacer is attached to a location of a plate and the attachment to that location is maintained during a CROF (i.e. the location of the spacer on respective plate does not change). An example of "a spacer is fixed with its respective plate" is that a spacer is monolithically made of one piece of material of the plate, and the location of the spacer relative to the plate surface does not change during CROF. An example of "a spacer is not fixed with its respective plate" is that a spacer is glued to a plate by an adhesive, but during a use of the plate, during CROF, the adhesive cannot hold the spacer at its original location on the plate surface and the spacer moves away from its original location on the plate surface.

The term "a spacer is fixed to a plate monolithically" means the spacer and the plate behavior like a single piece of an object where, during a use, the spacer does not move or separated from its original location on the plate.

The term "open configuration" of the two plates in a CROF process means a configuration in which the two plates are either partially or completely separated apart and the spacing between the plates is not regulated by the spacers The term "closed configuration" of the two plates in a CROF process means a configuration in which the plates are facing each other, the spacers and a relevant volume of the sample are between the plates, the thickness of the relevant volume of the sample is regulated by the plates and the spacers, wherein the relevant volume is at least a portion of an entire volume of the sample.

The term "a sample thickness is regulated by the plate and the spacers" in a CROF process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a CROF device refers to the surface of the plate that touches the sample, while the other surface (that does not touch the sample) of the plate is termed "outer surface".

The term "X-Plate" of a CROF device refers to a plate that comprises spaces that are on the sample surface of the plate, wherein the spacers have a predetermined inter-spacer distance and spacer height, and wherein at least one of the spacers is inside the sample contact area.

The term "CROF device" refers to a device that performs a CROF process. The term "CROFed" means that a CROF process is used. For example, the term "a sample was CROFed" means that the sample was put inside a CROF device, a CROF process was performed, and the sample was hold, unless stated otherwise, at a final configuration of the CROF.

The term "CROF plates" refers to the two plates used in performing a CROF process.

The term "surface smoothness" or "surface smoothness variation" of a planar surface refers to the average deviation of a planar surface from a perfect flat plane over a short distance that is about or smaller than a few micrometers. The surface smoothness is different from the surface flatness variation. A planar surface can have a good surface flatness, but poor surface smoothness.

The term "surface flatness" or "surface flatness variation" of a planar surface refers to the average deviation of a planar surface from a perfect flat plane over a long distance that is about or larger than 10 um. The surface flatness variation is different from the surface smoothness. A planar surface can have a good surface smoothness, but poor surface flatness (i.e., large surface flatness variation).

The term "relative surface flatness" of a plate or a sample is the ratio of the plate surface flatness variation to the final sample thickness.

The term "final sample thickness" in a CROF process refers to, unless specified otherwise, the thickness of the sample at the closed configuration of the plates in a CORF process.

The term "compression method" in CROF refers to a method that brings two plates from an open configuration to a closed configuration.

The term of "interested area" or "area of interest" of a plate refers to the area of the plate that is relevant to the function that the plates perform.

The term "at most" means "equal to or less than". For example, a spacer height is at most 1 um, it means that the spacer height is equal to or less than 1 um.

The term "sample area" means the area of the sample in the direction approximately parallel to the space between the plates and perpendicular to the sample thickness.

The term "sample thickness" refers to the sample dimension in the direction normal to the surface of the plates that face each other (e.g., the direction of the spacing between the plates).

The term "plate-spacing" refers to the distance between the inner surfaces of the two plates.

The term "deviation of the final sample thickness" in a CROF means the difference between the predetermined spacer height (determined from fabrication of the spacer)

and the average of the final sample thickness, wherein the average final sample thickness is averaged over a given area (e.g. an average of 25 different points (4 mm apart) over 1.6 cm by 1.6 cm area).

The term "uniformity of the measured final sample thickness" in a CROF process means the standard deviation of the measured final sample thickness over a given sample area (e.g. the standard deviation relative to the average.).

The term "relevant volume of a sample" and "relevant area of a sample" in a CROF process refers to, respectively, the volume and the area of a portion or entire volume of the sample deposited on the plates during a CROF process, that is relevant to a function to be performed by a respective method or device, wherein the function includes, but not limited to, reduction in binding time of analyte or entity, detection of analytes, quantify of a volume, quantify of a concentration, mixing of reagents, or control of a concentration (analytes, entity or reagents).

The term "some embodiments", "in some embodiments" "in the present invention, in some embodiments", "embodiment", "one embodiment", "another embodiment", "certain embodiments", "many embodiments", or alike refers, unless specifically stated otherwise, to an embodiment(s) that is (are) applied to the entire disclosure (i.e. the entire invention).

The term "height" or "thickness" of an object in a CROF process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a CROF process refers to, unless specifically stated, the area of the object that is parallel to a surface of the plate. For example, spacer area is the area of the spacer that is parallel to a surface of the plate.

The term "lateral" or "laterally" in a CROF process refers to, unless specifically stated, the direction that is parallel to a surface of the plate.

The term "width" of a spacer in a CROF process refers to, unless specifically stated, a lateral dimension of the spacer.

The term "a spacer inside a sample" means that the spacer is surrounded by the sample (e.g. a pillar spacer inside a sample).

The term "critical bending span" of a plate in a CROF process refers the span (i.e. distance) of the plate between two supports, at which the bending of the plate, for a given flexible plate, sample, and compression force, is equal to an allowed bending. For example, if an allowed bending is 50 nm and the critical bending span is 40 um for a given flexible plate, sample, and compression force, the bending of the plate between two neighboring spacers 40 um apart will be 50 nm, and the bending will be less than 50 nm if the two neighboring spacers is less than 40 um.

The term "flowable" for a sample means that when the thickness of the sample is reduced, the lateral dimension increases. For an example, a stool sample is regarded flowable.

In some embodiments of the present invention, a sample under a CROF process do not to be flowable to benefit from the process, as long as the sample thickness can be reduced under a CROF process. For an example, to stain a tissue by put a dye on a surface of the CROF plate, a CROF process can reduce the tissue thickness and hence speed up the saturation incubation time for staining by the dye.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. Nos. 62/456,065, filed on Feb. 7, 2017, which is incorporated herein in its entirety for all purposes.

Further aspects of the present disclosure include a CROF device that includes a plurality of capture agents that each binds to a plurality of analytes in a sample, i.e., a multiplexed CROF device. In such instances, the CROF device containing a plurality of capture agents can be configured to detect different types of analytes (protein, nucleic acids, antibodies, pathogens, etc.). The different analytes can be distinguishable from each other on the array based on the location within the array, the emission wavelength of the detectable label that binds to the different analytes, or a combination of the above.

Health conditions that can be diagnosed or measured by the subject method, device and system include, for example: chemical balance; nutritional health; exercise; fatigue; sleep; stress; prediabetes; allergies; aging; exposure to environmental toxins, pesticides, herbicides, synthetic hormone analogs; pregnancy; menopause; and andropause.

In certain embodiments, relative levels of nucleic acids in two or more different nucleic acid samples can be obtained using the above methods, and compared. In these embodiments, the results obtained from the above-described methods are usually normalized to the total amount of nucleic acids in the sample (e.g., constitutive RNAs), and compared. This can be done by comparing ratios, or by any other means. In particular embodiments, the nucleic acid profiles of two or more different samples can be compared to identify nucleic acids that are associated with a particular disease or condition.

In some examples, the different samples can consist of an "experimental" sample, i.e., a sample of interest, and a "control" sample to which the experimental sample can be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell can be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) can be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

Control and Measure the Sample Thickness without Using Spacers

In some embodiments of the present invention, the spacers that are used to regulate the sample or a relevant volume of the sample are replaced by (a) positioning sensors that can measure the plate inner spacing, and (b) the devices that can control the plate positions and move the plates into a desired plate inner spacing based on the information provided the sensors. In some embodiment, all the spacers are replaced by translation stage, monitoring sensors and feedback system. Measuring of Spacing and/or Sample Thickness Using Optical Method. In some embodiments, the measuring (f) of the spacing between the inner surfaces comprises the use of optical interference. The optical interference can use multiple wavelength. For example, the light signal due to the interference of a light reflected at the inner surface of the first plate and the second plate oscillate with the wavelength of the light. From the oscillation, one can determine the spacing between the inner surfaces. To enhance the interference signal, one of the inner surfaces or both can be coated with light reflection material.

In some embodiments, the measuring (f) of the spacing between the inner surfaces comprises taking optical imaging (e.g. taking a 2D (two-dimensional)/3D (three-dimensional) image of the sample and the image taking can be multiple times with different viewing angles, different wavelength, different phase, and/or different polarization) and image processing.
Measuring of Entire Sample Area or Volume Using Optical Methods. In some embodiments, the measuring (f) of the entire sample area or volume comprises taking optical imaging (e.g. taking a 2D (two-dimensional)/3D (three-dimensional) image of the sample and the image taking can be multiple times with different viewing angles, different wavelength, different phase, and/or different polarization) and image processing. The sample area means the area in the direction approximately parallel to the first plate and the second plate. The 3D imaging can use the method of fringe projection profilometry (FPP), which is one of the most prevalent methods for acquiring three-dimensional (3D) images of objects.
Assay Speed. In some embodiments, a release time control material is coated or mixed with a reagent on the plate, wherein the release time control material delay the time that reagent is released to the sample. In some embodiments, the release time control material delays the time that the dry regent is released into the blood sample by at least 3 seconds, e.g., at least 5 seconds or at least 10 seconds, or at least 20 seconds, or at least 60 seconds, or at least 90 seconds, or a value in the range of the two.

In some embodiments, the device is configured to analyze the sample in 60 seconds or less, 90 seconds or less, 120 seconds or less, 240 seconds or less, 300 seconds or less, or a value in the range of the two.

In some embodiments, at the closed configuration, the final sample thickness device is configured to analyze the sample in 60 seconds or less.

In some embodiments, at the closed configuration, the final sample thickness device is configured to the saturation time of the reagent with a sample in 10 seconds or less, 30 seconds or less, 60 seconds or less, 90 seconds or less, 120 seconds or less, 240 seconds or less, 300 seconds or less, or a value in the range of the two.
More Examples of QMAX Card. The method or device of any prior embodiment, wherein the spacers have pillar shape and nearly uniform cross-section.

The method or device of any prior embodiment, wherein the inter spacer distance (SD) is equal or less than about 120 um (micrometer).

The method or device of any prior embodiment, wherein the inter spacer distance (SD) is equal or less than about 100 um (micrometer).

The method or device of any prior embodiment, wherein the fourth power of the inter-spacer-distance (ISD) divided by the thickness (h) and the Young's modulus (E) of the flexible plate ($ISD^4/(hE)$) is $5 \times 10^6$ um$^3$/GPa or less.

The method or device of any prior embodiment, wherein the fourth power of the inter-spacer-distance (ISD) divided by the thickness (h) and the Young's modulus (E) of the flexible plate ($ISD^4/(hE)$) is $5 \times 10^5$ um$^3$/GPa or less.

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The method or device of any prior embodiment, wherein the spacers (e.g. the pillars) are periodic or aperiodic.

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate ($ISD^4/(hE)$) is $5 \times 10^6$ um$^3$/GPa or less.

The method or device of any prior embodiment, wherein the ratio of the inter-spacing distance of the spacers to the average width of the spacer is 2 or larger, and the filling factor of the spacers multiplied by the Young's modulus of the spacers is 2 MPa or larger.

The method or device of any prior embodiment, wherein the analytes is proteins, peptides, nucleic acids, synthetic compounds, or inorganic compounds.

The method or device of any prior embodiment, wherein the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

The method or device of any prior embodiment, wherein the spacers have a shape of pillars and a ratio of the width to the height of the pillar is equal or larger than one.

The method or device of any prior embodiment, wherein the sample that is deposited on one or both of the plates has an unknown volume.

The method or device of any prior embodiment, wherein the spacers have a shape of pillar, and the pillar has substantially uniform cross-section.

The method or device of any prior embodiment, wherein the samples is for the detection, purification and quantification of chemical compounds or biomolecules that correlates with the stage of certain diseases.

The method or device of any prior embodiment, wherein the samples is related to infectious and parasitic disease, injuries, cardiovascular disease, cancer, mental disorders, neuropsychiatric disorders, pulmonary diseases, renal diseases, and other and organic diseases.

The method or device of any prior embodiment, wherein the samples is related to the detection, purification and quantification of microorganism.

The method or device of any prior embodiment, wherein the samples is related to virus, fungus and bacteria from environment, e.g., water, soil, or biological samples.

The method or device of any prior embodiment, wherein the samples is related to the detection, quantification of chemical compounds or biological samples that pose hazard to food safety or national security, e.g. toxic waste, anthrax.

The method or device of any prior embodiment, wherein the samples is related to quantification of vital parameters in medical or physiological monitor.

The method or device of any prior embodiment, wherein the samples is related to glucose, blood, oxygen level, total blood count.

The method or device of any prior embodiment, wherein the samples is related to the detection and quantification of specific DNA or RNA from biosamples.

The method or device of any prior embodiment, wherein the samples is related to the sequencing and comparing of genetic sequences in DNA in the chromosomes and mitochondria for genome analysis.

The method or device of any prior embodiment, wherein the samples is related to detect reaction products, e.g., during synthesis or purification of pharmaceuticals.

The method or device of any prior embodiment, wherein the samples is cells, tissues, bodily fluids, and stool.

The method or device of any prior embodiment, wherein the sample is the sample in the fields of human, veterinary, agriculture, foods, environments, and drug testing.

The method or device of any prior embodiment, wherein the sample is a biological sample is selected from hair, finger nail, ear wax, breath, connective tissue, muscle tissue, nervous tissue, epithelial tissue, cartilage, cancerous sample, or bone.

The method or device of any prior embodiment, wherein the inter-spacer distance is in the range of 5 um to 120 um.

The method or device of any prior embodiment, wherein the inter-spacer distance is in the range of 120 um to 200 um.

The method or device of any prior embodiment, wherein the flexible plates have a thickness in the range of 20 um to 250 um and Young's modulus in the range 0.1 to 5 GPa.

The method or device of any prior embodiment, wherein for a flexible plate, the thickness of the flexible plate times the Young's modulus of the flexible plate is in the range 60 to 750 GPa-um.

The method or device of any prior embodiment, wherein the layer of uniform thickness sample is uniform over a lateral area that is at least 1 $mm^2$.

The method or device of any prior embodiment, wherein the layer of uniform thickness sample is uniform over a lateral area that is at least 3 $mm^2$.

In some embodiments, the measuring of the sample area or volume by imaging comprises (a) calibration of the image scale by using a sample of the known area or volume (e.g., The imager is a smartphone and the dimensions of the image taken by the phone can be calibrated by comparing an image of the a sample of known dimension taken the same phone); (b) comparison of the image with the scale markers (rulers) placed on or near the first plate and second plate (discussed further herein), and (c) a combination of thereof.

As used herein, light can include visible light, ultraviolet light, infrared light, and/or near infrared light. Light can include wavelengths in the range from 20 nm to 20,000 nm.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, reference to "an agent" includes a single agent and multiple agents, and reference to "a camera" includes a single camera and multiple cameras.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function can additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entity specifically identified. Thus, as a non-limiting example, a reference to "A and/or B," when used in conjunction with open-ended language such as "comprising" may refer, in some embodiments, to A only (optionally including entity other than B); in certain embodiments, to B only (optionally including entity other than A); in yet certain embodiments, to both A and B (optionally including other entity). These entities may refer to elements, actions, structures, steps, operations, values, and the like.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

It is believed that the following claims particularly point out certain combinations and sub-combinations that are directed to one of the disclosed inventions and are novel and non-obvious. Inventions embodied in other combinations and sub-combinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

What is claimed is:

1. A device for homogenous assay with particles aggregation, comprising: a first plate, a second plate, spacers, and a plurality of separated particles, wherein:
   the plates are movable relative to each other into different configurations, including an open configuration and a closed configuration;
   each of the plates has, on its respective inner surface, a sample contact area for contacting a sample that contains or is suspected to contain an analyte;
   one or both of the plates comprise, inside the sample contact area, one or more spacers of predetermined substantially uniform height of 200 µm or less;
   one or both of the plates comprise, on the respective inner surface, the plurality of separated particles, wherein the particles have capture agents immobilized thereon, wherein the capture agents are capable of binding to and immobilizing the analyte and causing, after binding to the analyte, an aggregation of the separated particles;
   in the open configuration, the two plates are partially or entirely separated apart, the spacing between the plates is not regulated by the spacers, and the sample is deposited on one or both of the plates; and
   in the closed configuration, which is configured after deposition of the sample in the open configuration, at least part of the sample is compressed by the two plates into a layer of highly uniform thickness, the uniform thickness of the layer is confined by the inner surfaces of the plates and is regulated by the plates and the spacers; and the ratio of the sample thickness to the diameter of the particle is less than 200.

2. The device of claim 1, wherein the particles are different in their optical properties selected from the group consisting of: photoluminescence, electroluminescence, and electrochemiluminescence, light absorption, reflection, transmission, diffraction, scattering, diffusion, surface Raman scattering, and any combination thereof.

3. The device of claim 1, wherein the particles are biological/nonbiological, organic/non-organic, magnetic/non-magnetic, metallic/non-metallic, light-emitting/non-emitting, or a combination thereof.

4. The device of claim 1, wherein the particles are natural biological entities selected from cells, cell fragments, macromolecules, polysaccharides, proteins, nucleic acids, cell congregates, tissues, virus particles, or a mixture thereof.

5. The device of claim 1, wherein the particles are selected from polymer particles, metal particles, magnetic particles, semiconductor particles, or a combination or mixtures thereof.

6. The device of claim 1, wherein the particles are a polymer selected from polystyrene, polypropylene, polycarbonate, latex, or any combinations thereof.

7. The device of claim 1, wherein the particles are metal particles selected from, silver, copper, platinum, or a mixture thereof.

8. The device of claim 1, wherein the particles are gold nanoparticles, gold nanoshell particles, gold nanotube particles, or a mixture thereof.

9. The device of claim 1, wherein the particles are a semiconductor selected from CdSe, CdS, CdS coated with ZnS, CdSe coated with ZnS, or a mixture thereof.

10. The device of claim 1, wherein the particles are magnetic selected from ferromagnetite, magnetized ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, GaAs, or a mixture thereof.

11. The device of claim 1, wherein the particles have a shape, selected from spheres, beads, rods, irregular shapes, or a combination thereof.

12. The device of claim 1, wherein a population of the particles has particles having the same size or shape, particles having varying shapes or sizes, or a mixture thereof.

13. The device of claim 1, wherein the particles are nanoparticles that have a size in the nanometer range; the particles are microparticles that have a size in the micrometer level, or a mixture thereof.

14. The device of claim 1, wherein the particles have a size selected from about 5 nm to about 10 µm.

15. The device of claim 1, wherein the particles have a size from 500 nm to 5 µm.

16. The device of claim 1, wherein the spacer height, the spacing between the plates, the sample thickness, or any combination thereof, is from 1 µm to 10 µm.

17. The device of claim 1, wherein the spacer height, the spacing between the plates, the sample thickness, or any combination thereof, is from 1 µm to 100 µm.

18. The device of claim 1, wherein the binding between the agents is selected from antibody-antigen binding, complimentary binding of nucleic acids, a binding between an catalyst and its substrate, a binding or aptamer against its target, a binding of an RNA interference sequence against its target, a ligand-receptor binding, or a binding between an agent and its agonist or antagonist.

19. The device of claim 1, wherein at the closed configuration, the final sample thickness device is configured to analyze the sample in 60 seconds or less.

20. The device of claim 1, wherein the plurality of separated particles are on the surface of the plate that has spacers.

21. The device of claim 1, wherein the spacer is 10 μm height and the particles are 1 μm diameter beads.

22. The device of claim 1, further comprising a dry reagent coated on one or both plates.

23. The device of claim 1, wherein the samples are related to infectious and parasitic disease, injuries, cardiovascular disease, cancer, mental disorders, neuropsychiatric disorders, pulmonary diseases, renal diseases, and other and organic diseases.

24. The device of claim 1, wherein the samples are related to quantification of vital parameters in medical or physiological monitor.

25. The device of claim 1, wherein the sample is a sample for detection of proteins, peptides, nucleic acids, synthetic compounds, inorganic compounds.

26. The device of claim 1, wherein the sample is a sample in the fields of human, veterinary, agriculture, foods, environments, and drug testing.

27. The device of claim 1, wherein for a flexible plate, the fourth power of the inter-spacer-distance (ISD) divided by the thickness of the flexible plate (h) and the Young's modulus (E) of the flexible plate, $ISD^4/(hE)$, is equal to or less than $5 \times 10^6$ μm$^3$/GPa.

28. The device of claim 1, wherein the spacers are periodically arranged.

29. The device of claim 1, wherein the inter spacer distance (ISD) is equal or less than about 120 μm (micrometer).

30. A device for homogenous assay with particles aggregation, comprising: a first plate, a second plate, spacers, and a plurality of aggregated particles, wherein:
the plates are movable relative to each other into different configurations, including an open configuration and a closed configuration;
each of the plates has, on its respective inner surface, a sample contact area for contacting a sample that contains or is suspected to contain an analyte;
one or both of the plates comprise, inside the sample contact area, one or more spacers of predetermined substantially uniform height of 200 μm or less;
one or both of the plates comprise, on the respective inner surface, the plurality of aggregated particles, wherein the particles have binding agents connected to the surface of the particles; and wherein the analyte de-aggregates the aggregated particles when the analyte contacts the particles;
in the open configuration, the two plates are partially or entirely separated apart, the spacing between the plates is not regulated by the spacers, and the sample is deposited on one or both of the plates; and
in the closed configuration, which is configured after deposition of the sample in the open configuration, at least part of the sample is compressed by the two plates into a layer of highly uniform thickness, the uniform thickness of the layer is confined by the inner surfaces of the plates and is regulated by the plates and the spacers, and the ratio of the sample thickness to the diameter of the particle is less than 200.

31. A system for measuring an aggregation or de-aggregation of particles caused by an analyte, comprising:

the device of claim 30, a light source that emits light, and an imager, wherein the imager is configured to image the light that transmits through, scattered from, or reflected from the aggregated, the de-aggregated particles, or any combination of thereof.

32. The device of claim 30, wherein the binding agents and the particles are coated or surface modified with agents to enhance binding of a selected analyte.

33. The device of claim 30, wherein the particles are different in their optical properties selected from the group consisting of: photoluminescence, electroluminescence, and electrochemiluminescence, light absorption, reflection, transmission, diffraction, scattering, diffusion, surface Raman scattering, and any combination thereof.

34. The device of claim 30, wherein the particles are biological/nonbiological, organic/non-organic, magnetic/non-magnetic, metallic/non-metallic, light-emitting/non-emitting, or a combination thereof.

35. The device of claim 30, wherein the particles are natural biological entities selected from cells, cell fragments, macromolecules, polysaccharides, proteins, nucleic acids, cell congregates, tissues, virus particles, or a mixture thereof.

36. The device of claim 30, wherein the particles are selected from polymer particles, metal particles, magnetic particles, semiconductor particles, or a combination or mixtures thereof.

37. The device of claim 30, wherein the particles are a polymer selected from polystyrene, polypropylene, polycarbonate, latex, or any combinations thereof.

38. The device of claim 30, wherein the particles are metal particles selected from, silver, copper, platinum, or a mixture thereof.

39. The device of claim 30, wherein the particles are gold nanoparticles, gold nanoshell particles, gold nanotube particles, or a mixture thereof.

40. The device of claim 30, wherein the particles are a semiconductor selected from CdSe, CdS, CdS coated with ZnS, CdSe coated with ZnS, or a mixture thereof.

41. The device of claim 30, wherein the particles are magnetic selected from ferromagnetite, magnetized ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, GaAs, or a mixture thereof.

42. The device of claim 30, wherein the particles have a shape, selected from spheres, beads, rods, irregular shapes, or a combination thereof.

43. The device of claim 30, wherein a population of the particles has particles having the same size or shape, particles having varying shapes or sizes, or a mixture thereof.

44. The device of claim 30, wherein the particles are nanoparticles that have a size in the nanometer range; the particles are microparticles that have a size in the micrometer level, or a mixture thereof.

45. The device of claim 30, wherein the particles have a size selected from about 5 nm to about 10 μm.

46. The device of claim 30, wherein the particles have a size from 500 nm to 5 μm.

47. The device of claim 30, wherein the spacer height, the spacing between the plates, the sample thickness, or any combination thereof, is from 1 um to 10 μm.

48. The device of claim 30, wherein the spacer height, the spacing between the plates, the sample thickness, or any combination thereof, is from 1 μm to 100 μm.

49. The device of claim 30, wherein the binding between the agents is selected from antibody-antigen binding, complimentary binding of nucleic acids, a binding between an catalyst and its substrate, a binding or aptamer against its target, a binding of an RNA interference sequence against its target, a ligand-receptor binding, or a binding between an agent and its agonist or antagonist.

50. The device of claim 30, wherein at the closed configuration, the final sample thickness device is configured to analyze the sample in 60 seconds or less.

51. The device of claim 30, wherein the plurality of aggregated particles are on the surface of the plate that has spacers.

52. The device of claim 30, wherein the spacer is 10 μm height and the particles are 1 μm diameter beads.

53. The device of claim 30, further comprising a dry reagent coated on one or both plates.

54. The device of claim 30, wherein the samples are related to infectious and parasitic disease, injuries, cardiovascular disease, cancer, mental disorders, neuropsychiatric disorders, pulmonary diseases, renal diseases, and other and organic diseases.

55. The device of claim 30, wherein the samples are related to quantification of vital parameters in medical or physiological monitor.

56. The device of claim 30, wherein the sample is a sample for detection of proteins, peptides, nucleic acids, synthetic compounds, inorganic compounds.

57. The device of claim 30, wherein the sample is a sample in the fields of human, veterinary, agriculture, foods, environments, and drug testing.

58. The device of claim 30, wherein for a flexible plate, the fourth 30 power of the inter-spacer-distance (ISD) divided by the thickness of the flexible plate (h) and the Young's modulus (E) of the flexible plate, $ISD^4/(hE)$, is equal to or less than $5 \times 10^6$ μm$^3$/GPa.

59. The device of claim 30, wherein the spacers are periodically arranged.

60. The device of claim 30, wherein the inter spacer distance (ISD) is equal or less than about 120 μm (micrometer).

61. A method of performing a homogenous assay with particle aggregation, comprising:
   (a) providing a sample containing or suspected of containing an analyte;
   (b) providing a first plate and a second plate, wherein:
      i. the plates are movable relative to each other into different configurations, including an open configuration and a closed configuration;
      ii. each of the plates has, on its respective inner surface, a sample contact area for contacting the sample;
      iii. one or both of the plates comprise spacers, at least one of the spacers is inside the sample contact area, and the spacers have a predetermined substantially uniform height; and
      iv. one or both of the plates comprise, on the respective inner surface, a plurality of separated particles;
   (c) depositing the sample on one or both of the plates when the plates are in the open configuration, wherein in the open configuration, the two plates are partially or entirely separated apart and the spacing between the plates is not regulated by the spacers;
   (d) after (c), bringing the two plates together and pressing the plates into the closed configuration, wherein in the closed configuration: at least part of the sample is compressed by the two plates into a layer of highly uniform thickness, the uniform thickness of the layer is confined by the inner surfaces of the two plates and is regulated by the spacers and the plates; and
   (e) while the plates are at the closed configuration, imaging using an imager and analyzing the aggregated particles in the layer of uniform thickness.

62. The method of claim 61, wherein the imaging images a plasmonic resonance shift caused by angulation of the particles.

63. The method of claim 61, wherein the imager directly images the agglutination of particles.

64. A method of performing a homogenous assay with particle de-aggregation, comprising:
   (a) providing a sample containing or suspected of containing an analyte;
   (b) providing a first plate and a second plate, wherein:
      i. the plates are movable relative to each other into different configurations, including an open configuration and a closed configuration;
      ii. each of the plates has, on its respective inner surface, a sample contact area for contacting the sample;
      iii. one or both of the plates comprise spacers, at least one of the spacers is inside the sample contact area, and the spacers have a predetermined substantially uniform height;
      iv. one or both of the plates comprise, on the respective inner surface, a plurality of aggregated particles;
   (c) depositing the sample on one or both of the plates when the plates in the open configuration, wherein in the open configuration, the two plates are partially or entirely separated apart and the spacing between the plates is not regulated by the spacers;
   (d) after (c), bringing the two plates together and pressing the plates into the closed configuration, wherein in the closed configuration: at least part of the sample is compressed by the two plates into a layer of highly uniform thickness, the uniform thickness of the layer is confined by the inner surfaces of the two plates and is regulated by the spacers and the plates; and
   (e) while the plates are at the closed configuration, imaging, using an imager, and analyzing the de-aggregated particles in the layer of uniform thickness by image or lump sum optical signal.

65. The method of claim 64, wherein the imaging images a plasmonic resonance shift caused by angulation of the particles.

66. The method of claim 64, wherein the imager directly images the agglutination of particles.

* * * * *